(12) United States Patent
Tuttle

(10) Patent No.: US 10,740,857 B2
(45) Date of Patent: Aug. 11, 2020

(54) METHOD AND SYSTEM FOR ORDERING CUSTOM PROSTHETIC AND ORTHOPEDIC DEVICES

(71) Applicant: OSSUR HF, Reykjavik (IS)

(72) Inventor: Michael Patrick Tuttle, Titusville, FL (US)

(73) Assignee: OSSUR HF, Reykjavik (IS)

( * ) Notice: Subject to any disclaimer, the term of this patent is extended or adjusted under 35 U.S.C. 154(b) by 1178 days.

(21) Appl. No.: 14/644,923

(22) Filed: Mar. 11, 2015

(65) Prior Publication Data

US 2015/0262319 A1 Sep. 17, 2015

Related U.S. Application Data

(60) Provisional application No. 61/951,180, filed on Mar. 11, 2014.

(51) Int. Cl.
*G06Q 50/22* (2018.01)
*G06Q 30/06* (2012.01)
(Continued)

(52) U.S. Cl.
CPC ........... *G06Q 50/22* (2013.01); *A61F 2/5046* (2013.01); *A61F 5/01* (2013.01); *G06Q 30/0621* (2013.01); *G06Q 30/0633* (2013.01); *G06T 17/00* (2013.01); *G16H 50/50* (2018.01); *H04N 13/204* (2018.05); *H04N 13/275* (2018.05); *G06T 2210/41* (2013.01)

(58) Field of Classification Search
CPC ....... G06Q 50/24; G06F 19/321; G06F 19/12; G06F 3/0346; G06F 19/3418; G06F 16/5854; G06T 2207/30008; G06T 1/0007; G06T 19/20; G06T 2200/08; G06T 1/00; A61B 2034/105; A61B 2034/108; A61B 6/505; A61B 2034/2068; A61B 2090/364
USPC ....................................................... 705/2, 3
See application file for complete search history.

(56) References Cited

U.S. PATENT DOCUMENTS 2,318,864 A 5/1943 Jackson
2,980,110 A 4/1961 Brumfield et al.
(Continued)

FOREIGN PATENT DOCUMENTS

WO 2013/058978 A1 4/2013
WO 2013/071416 A1 5/2013

OTHER PUBLICATIONS

International Search Report from International Application No. PCT/US2015/019937, dated May 18, 2015.
(Continued)

*Primary Examiner* — Victoria P Augustine
*Assistant Examiner* — Teresa S Williams
(74) *Attorney, Agent, or Firm* — Workman Nydegger

(57) ABSTRACT

A method of ordering a custom prosthetic or orthopedic device includes manually moving a portable scanner about an anatomical part of a patient to generate three-dimensional information representative of the anatomical part. The portable scanner is coupled to a mobile device routinely carried by a user. The method involves obtaining order information associated with the patient on the mobile device and transmitting an order with the mobile device to an intended recipient. The order contains at least a portion of the three-dimensional information and at least a portion of the order information.

21 Claims, 6 Drawing Sheets

(51) Int. Cl.
| | |
|---|---|
| *G16H 50/50* | (2018.01) |
| *H04N 13/204* | (2018.01) |
| *H04N 13/275* | (2018.01) |
| *G06T 17/00* | (2006.01) |
| *A61F 2/50* | (2006.01) |
| *A61F 5/01* | (2006.01) |

(56) References Cited

U.S. PATENT DOCUMENTS

| | | | |
|---|---|---|---|
| 3,008,239 | A | 11/1961 | Lange |
| 3,140,546 | A | 7/1964 | Bartlett |
| 3,953,900 | A | 5/1976 | Thompson |
| 4,315,372 | A | 2/1982 | Kinkead |
| 4,776,327 | A | 10/1988 | Russell |
| 4,807,605 | A | 2/1989 | Mattingly |
| 4,827,916 | A | 5/1989 | Kosova |
| 5,443,510 | A | 8/1995 | Shetty et al. |
| 5,556,373 | A | 9/1996 | Motloch |
| 5,662,594 | A | 9/1997 | Rosenblatt |
| 5,741,215 | A | 4/1998 | D'Urso |
| 5,768,134 | A | 6/1998 | Swaelens et al. |
| 5,857,987 | A | 1/1999 | Habermeyer |
| 5,880,964 | A | 3/1999 | Schall et al. |
| 5,886,775 | A | 3/1999 | Houser et al. |
| 5,888,216 | A | 3/1999 | Haberman |
| 6,236,743 | B1 | 5/2001 | Pratt |
| 6,427,695 | B1 | 8/2002 | Zanetti et al. |
| 6,463,351 | B1 | 10/2002 | Clynch |
| 6,540,708 | B1 | 4/2003 | Manspeizer |
| 6,564,086 | B2 | 5/2003 | Marchitto et al. |
| 6,572,571 | B2 | 6/2003 | Lowe |
| 6,597,965 | B2 | 7/2003 | Graves et al. |
| 6,613,006 | B1 | 9/2003 | Asherman |
| 6,725,118 | B1 | 4/2004 | Fried et al. |
| 6,726,641 | B2 | 4/2004 | Chiang et al. |
| 6,968,246 | B2 | 11/2005 | Watson et al. |
| 7,127,101 | B2 | 10/2006 | Littlefield et al. |
| 7,210,926 | B2 | 5/2007 | Tadros et al. |
| 7,242,798 | B2 | 7/2007 | Littlefield et al. |
| 7,340,316 | B2 * | 3/2008 | Spaeth ............... A61B 5/0064 700/98 |
| 7,661,170 | B2 | 2/2010 | Goode et al. |
| 7,797,072 | B2 | 9/2010 | Summit |
| 7,896,827 | B2 | 3/2011 | Ingimundarson et al. |
| 8,005,651 | B2 | 8/2011 | Summit et al. |
| 8,059,917 | B2 | 11/2011 | Dumas et al. |
| 8,613,716 | B2 | 12/2013 | Summit et al. |
| 8,908,928 | B1 * | 12/2014 | Hansen ............. G06K 9/00362 382/111 |
| 2001/0002232 | A1 | 5/2001 | Young et al. |
| 2002/0016631 | A1 | 2/2002 | Marchitto et al. |
| 2003/0032906 | A1 | 2/2003 | Narula et al. |
| 2003/0065259 | A1 | 4/2003 | Gateno et al. |
| 2004/0019266 | A1 | 1/2004 | Marciante et al. |
| 2004/0068337 | A1 | 4/2004 | Watson et al. |
| 2004/0133431 | A1 | 7/2004 | Udiljak et al. |
| 2004/0162511 | A1 | 8/2004 | Barberio |
| 2004/0230149 | A1 | 11/2004 | Littlefield et al. |
| 2004/0236424 | A1 | 11/2004 | Berez et al. |
| 2004/0260402 | A1 | 12/2004 | Baldini et al. |
| 2005/0004472 | A1 | 1/2005 | Pratt |
| 2005/0015172 | A1 | 1/2005 | Fried et al. |
| 2005/0043835 | A1 | 2/2005 | Christensen |
| 2005/0061332 | A1 | 3/2005 | Greenawalt et al. |
| 2005/0065458 | A1 | 3/2005 | Kim |
| 2006/0100832 | A1 | 5/2006 | Bowman |
| 2006/0161267 | A1 | 7/2006 | Clausen |
| 2007/0016323 | A1 | 1/2007 | Fried |
| 2007/0133850 | A1 | 6/2007 | Paez |
| 2007/0172112 | A1 | 7/2007 | Paley et al. |
| 2007/0225630 | A1 | 9/2007 | Wyatt et al. |
| 2008/0120756 | A1 | 5/2008 | Shepherd |
| 2008/0294083 | A1 | 11/2008 | Chang et al. |
| 2008/0319362 | A1 | 12/2008 | Joseph |
| 2009/0088674 | A1 | 4/2009 | Caillouette et al. |
| 2009/0254015 | A1 | 10/2009 | Segal et al. |
| 2009/0306801 | A1 * | 12/2009 | Sivak ................ A61F 5/0111 700/98 |
| 2010/0008588 | A1 | 1/2010 | Feldkhun et al. |
| 2010/0137770 | A1 | 6/2010 | Ingimundarson et al. |
| 2010/0138193 | A1 | 6/2010 | Summit et al. |
| 2010/0228646 | A1 | 9/2010 | Heidel |
| 2010/0268138 | A1 | 10/2010 | Summit et al. |
| 2011/0001983 | A1 | 1/2011 | Becker et al. |
| 2011/0054486 | A1 | 3/2011 | Linder-Ganz et al. |
| 2011/0056004 | A1 | 3/2011 | Landi |
| 2011/0166435 | A1 | 7/2011 | Lye |
| 2014/0126770 | A1 * | 5/2014 | Odessky ............... G06F 19/321 382/103 |
| 2014/0157579 | A1 * | 6/2014 | Chhabra ................ G06F 17/00 29/592 |
| 2018/0153716 | A1 | 6/2018 | Martin |

OTHER PUBLICATIONS

"Digital Measuring System for Unloader & Cti CM Braces", Ossur; Aug. 1, 2012, 3 pages.

"OMEGA: OMEGA Tracer is the most versatile CAD/CAM technology for the orthotic and prosthetic industry." Downloaded from https://web.archive.org/web/20130513201657/http://www.willowwoodco.com/products-and-services/ omega, May 13, 2013, 42 pages.

International Search Report from International Search Application No. PCT/US13/56896, dated Apr. 23, 2014.

Summons to Attend Oral Proceedings from EP Application No. EP 15711408.3, dated May 14, 2018.

* cited by examiner

METHOD AND SYSTEM FOR ORDERING CUSTOM PROSTHETIC AND ORTHOPEDIC DEVICES

TECHNICAL FIELD

The disclosure relates to a method and system for ordering custom prosthetic or orthopedic devices.

BACKGROUND

Many functions in the conventional ordering and design of custom prosthetic and orthopedic devices are performed by hand. For instance, a patient will typically have a prosthetic socket made through a provider (e.g., a prosthetist) having the expertise to assure that the socket fits properly. The patient is typically required to travel to the provider's facility where a handmade plaster cast of the patient's residual limb is created. The patient's personal information is then recorded and both the handmade plaster cast and the patient's personal information are then transported or mailed to a fabricating facility.

At the fabricating facility, the patient's personal information is entered into the fabricator's system and the plaster cast is processed and used to generate fitting information. The fabricator then forms the custom prosthetic socket according to the fitting information obtained from the plaster cast. Similar processes are used by orthotist and fabricators in the ordering of custom orthopedic devices or orthosis where patient information is obtained, handmade plaster casts are created, transported, and processed to generate fitting information.

Conventional systems such as these tend to suffer from a number of drawbacks. For instance, the casting and fitting process can require significant travel and/or require the patient to be at the provider's facility for lengthy periods of time. This can be both inconvenient and expensive for the patient. In addition, forming a custom prosthetic or orthopedic device based on a handmade plaster cast can be uncomfortable and imprecise, resulting in a poor and potentially damaging fit. These systems also can take days, weeks, or even months to fabricate the custom device and can include postal delays. Moreover, handmade plaster casts have a tendency to deform during transport, which in turn, can generate faulty fitting information and a poor fit. These systems also require manual data entry at multiple locations and times, which is often tedious and susceptible to human error.

Some efforts have been made to use computer animated design and scanners at dedicated facilities to generate patient fitting information for ordering purposes; however, such systems are stationary, expensive, limited geographically, uncomfortable, and inconvenient for the patient.

There is a need for a method and system for ordering custom prosthetic and/or orthopedic devices that is versatile, affordable, portable, and provides more accurate fitting information.

SUMMARY

According to a method for ordering a custom prosthetic or orthopedic device, the method includes manually moving a portable scanner about an anatomical part of a patient to generate three-dimensional information representative of the anatomical part. The portable scanner is coupled to a mobile device routinely carried by a user. The method involves obtaining order information associated with the patient on the mobile device and transmitting an order with the mobile device to an intended recipient. The order contains at least a portion of the three-dimensional information and at least a portion of the order information.

Creating the order with the portable scanner and mobile device can be performed virtually anywhere as compared to the prior art where orders for custom prosthetic and orthopedic devices are generated at dedicated facilities with cumbersome and stationary equipment and/or casting capabilities. This advantageously provides a user and/or patient with significant freedom. For instance, the order can be created at the patient's home, in a hospital room, in a community center, in the field, on a humanitarian mission, off the power grid, and/or in other settings around the world, substantially eliminating the need of extensive facilities.

It advantageously also provides more accurate fitting information than in the prior art where three-dimensional information or fitting information is obtained from a plaster cast, substantially decreasing the likelihood of a poor fitting prosthetic or orthopedic device. It also eliminates the likelihood of a plaster cast deforming during transport, which, in turn, can generate faulty fitting information and a poor fit. It also avoids the discomfort and inconveniences that can result when plaster casts are made of the anatomical part.

Generating the three-dimensional information using the portable scanner and mobile device also eliminates the need to convert information obtained from a physical mold to three-dimensional information representative of the anatomical part, which, in turn, reduces labor, cost, and time. Further, transmitting an order including the three-dimensional and order information with the mobile device to the intended recipient eliminates the need to manually enter or record information contained in the order at multiple location, which is often tedious and susceptible to human error. It also shortens the overall time to complete the ordering of a prosthetic or orthopedic device.

According to a variation, the order is encrypted before transmitting the order to the intended recipient. This helps protect the patient's privacy and ensures that only the intended recipient is capable of deciphering private and/or necessary details from the order.

BRIEF DESCRIPTION OF THE DRAWINGS

These and other features, aspects, and advantages of the present disclosure will become better understood regarding the following description, appended claims, and accompanying drawings.

FIG. 6 is an ordering environment according to another embodiment.

FIG. 7 is an ordering environment according to another embodiment.

FIG. 8 is an ordering environment according to another environment.

DETAILED DESCRIPTION OF VARIOUS EMBODIMENTS

Figure 1:
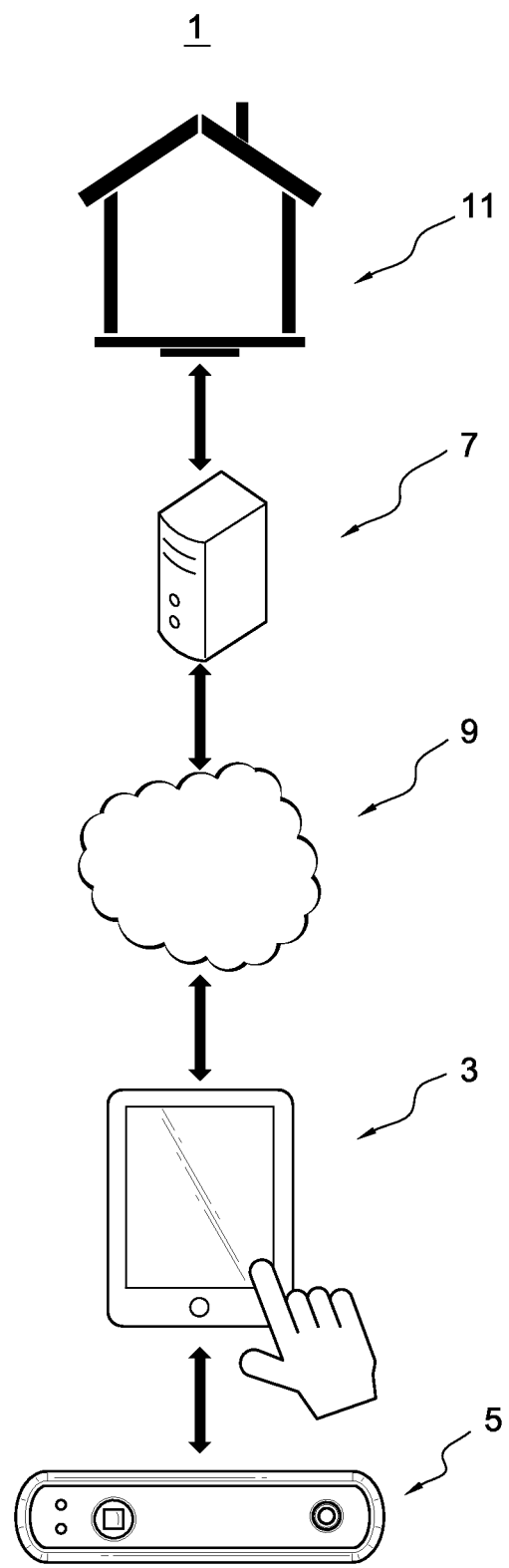
FIG. 1 is an architectural schematic diagram of a system for ordering a custom prosthetic or orthopedic device according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

FIG. 1 schematically depicts a system 1 for ordering a custom orthopedic or prosthetic device. The depicted system 1 includes a computer device 3 that can display information to a user and receive user input, respectively. The computer device 3 is communicatively coupled to at least one digital imaging device 5. The digital imaging device 5 can communicate with the computer device 3 and can be moved manually about an anatomical part of a patient such that three-dimensional information representative of the anatomical part can be generated for fitting purposes. The three-dimensional information can include a three-dimensional image, a digital capture, a three-dimensional scan, a captured scan, a three-dimensional data set, combinations thereof, or other appropriate information. The three-dimensional information can include relative position, surface contour, shape, volume, or other information.

As seen, the computer device 3 preferably is a mobile device 3. A mobile device is defined as a processing device routinely carried by a user, as opposed to a processing device such as a desktop computer which is not routinely carried by a user. It typically has a display screen with touch input and/or a keyboard, and its own power source. As such, the mobile device 3 can provide a user the freedom to use the mobile device 3 almost anywhere. The mobile device 3 can be a hand-held device. The mobile device 3 can be a tablet computer, a smartphone, a laptop, a mobile telephone, a PDA, or other appropriate device. It will be appreciated that any of the methods and systems described herein may be adapted to couple the digital imaging device 5 to a computer device such as a desktop computer or the like in place of the mobile device.

The digital imaging device 5 preferably is a portable scanner 5. As used herein, the term "portable" means a device or system able to be easily carried or moved, especially one that is lightweight and/or designed for portability. The portable scanner 5 can includes its own power source. The portable scanner 5 can be a three-dimensional sensor. The portable scanner 5 can be a Kinect®, a Structure Sensor®, or another suitable type of portable three-dimensional sensor. The portable scanner 5 can be separate or remote from the computer device 3. The portable scanner 5 can be attached to or incorporated in the mobile device 3.

The lightweight and portable nature of the mobile device 3 and portable scanner 5 advantageously makes them very versatile, convenient to travel with, and easy to quickly scan the patient virtually anywhere, providing significant freedom to a user. For instance, the mobile device 3 and the portable scanner 5 can be used in the ordering of custom prosthetic and orthopedic devices at a patient's home, in a hospital room, at a community clinic, in remote locations, and in other settings. In short, the mobile device 3 and portable scanner 5 can be, for example, placed in a bag and taken almost anywhere to fit a patient for a custom prosthetic or orthopedic device. This is advantageous over the prior art where the patient is required to visit a designated facility with big, cumbersome, and stationary equipment and/or casting capabilities to be fitted for a custom prosthetic or orthopedic device, requiring significant time and money and in many instances proving impossible for patients living in remote locations.

Optionally, the mobile device 3 can be communicatively coupled to a server or computer system 7 over a network 9, such as for example, a Local Area Network ("LAN"), a Wide Area Network ("WAN"), and even the internet. The computer system 7 can be located remotely from the mobile device 3. The computer system 7 can be used for controlling/monitoring the mobile device 3 and/or portable scanner 5. The computer system 7 can be used for exchanging information/files with the mobile device 3 and/or portable scanner 5. For instance, the mobile device 3 can send one or more order files including user information and three-dimensional information representative of the patient's anatomical part to the computer system 7 of an intended recipient at a remote facility 11. In some embodiments, the intended recipient can use the order file to obtain fitting information for the patient. The intended recipient then can form or fabricate a prosthetic or orthopedic device according to the fitting information obtained from the order file.

The exact division of labor between mobile device 3 and computer system 7 may vary. At one end of the spectrum, the computer system 7 performs nearly all operations and the mobile device 3 merely carries out instructions that are received from the computer system 7. At the other end of the spectrum, the computer system 7 receives and stores data/files from the mobile device 3, and the mobile device 3 performs all other operations. Any division of labor along this spectrum is also within the scope of the present disclosure.

Figure 2:
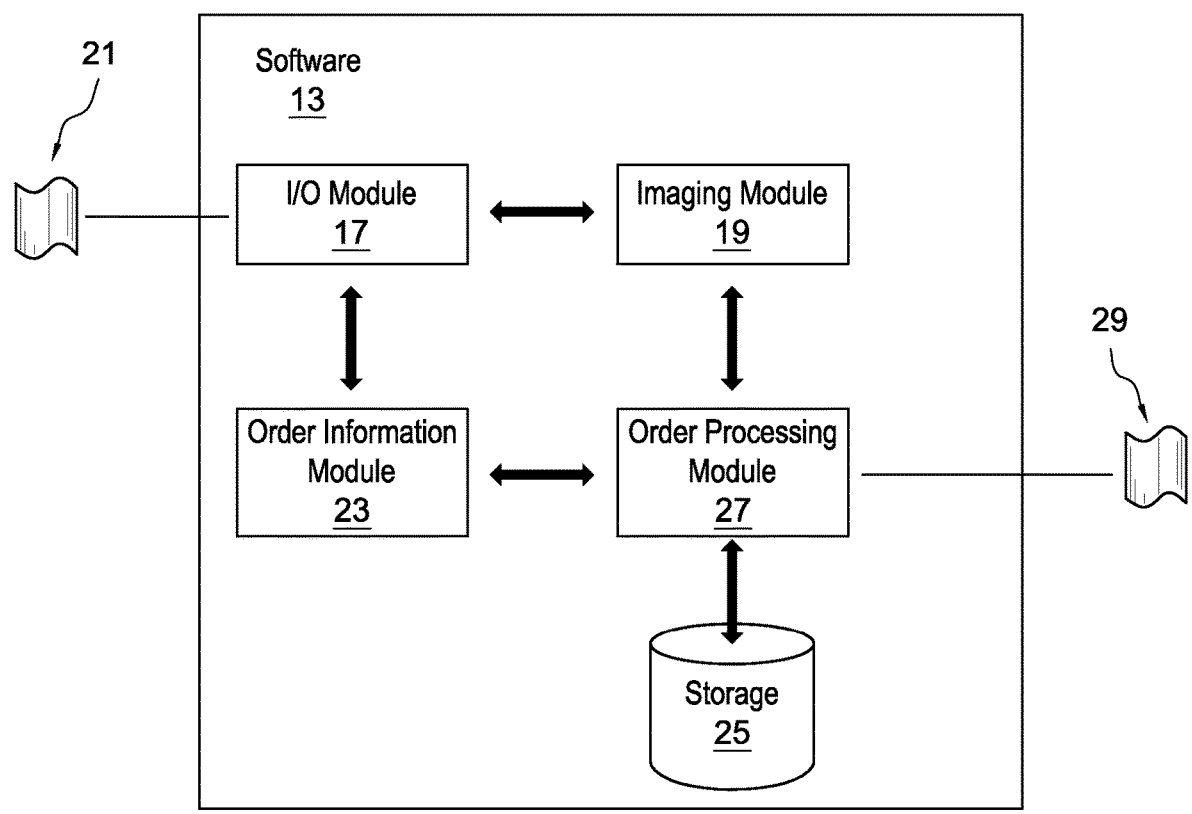
FIG. 2 is another architectural schematic diagram of the system shown in FIG. 1.

As seen in FIG. 2, the mobile device 3 and the portable scanner 5 can be in communication with ordering software 13. The ordering software 13 may be embodied on a computer readable medium which when executed by a processor of the mobile device 3 performs a sequence of steps. The ordering software 13 may be a mobile application or application software configured to specifically run on mobile devices. The ordering software 13 may be a web-based programming language and/or web-based computing platform. The ordering software 13 may be a computer programming language that is concurrent, class-based, object oriented, and designed to have minimal implementation dependencies (e.g., Java programming language).

The ordering software 13 can be executed on a computer to provide a user with an ordering environment described below. The ordering software 13 can be executed on a single device such as the mobile device 3 or the computer system 7. The ordering software 13 can be executed on a combination of devices such as the mobile device 3 and the computer system 7. The ordering software 13 can be executed in a distributed computer environment. For instance, various modules of the ordering software 13 may be executed in whole or in part by the mobile device 3, the portable scanner 5, the computer system 7, and/or other computer systems.

Once executed, the mobile device 3 and the portable scanner 5 both communicate with the I/O module 17. The I/O module 17 can direct the mobile device 3 to show various aspects of the ordering environment 15 and can receive instructions and commands from a user and/or other devices.

When receiving inputs from a user, the I/O module 17 can communicate relevant commands to other modules within the ordering software 13. As such, the ordering software 13 can provide a user with a variety of different options, including, but not limited to, a scanning option, an order information entry option, and sending option.

For example, the I/O module 17 can receive instructions from a user to scan an anatomical part of a patient. Upon receiving the instructions, the I/O module 17 communicates the relevant commands to an imaging module 19. Through the I/O module, the imaging module 19 can direct the portable scanner 5 to scan or image the anatomical part and can receive data 21 from the portable scanner 5. During scanning, a user can circumferentially position the portable scanner 5 around the anatomical part. Because of the portable nature of the portable scanner 5 and mobile device 3, the user can scan the anatomical part virtually anywhere rather being tied down to a designated clinic or facility as in the prior art, providing significant freedom to the user and patient.

The imaging module 19 can use the data 21 to obtain three-dimensional information representative of the anatomical part and/or generate an image or rendered model representative of the three-dimensional information, which, in turn, can provide fitting information for a custom prosthetic or orthopedic device. The I/O module 17 can display the rendered model or image to the user.

When a user is satisfied with the rendered model, the user can access functions of an order information module 23. The order information module 23 can provide a user with a variety of different options for entering patient data, including, but not limited to, a shipping information form, a patient information form, a socket selection form, and a billing information form. Once a user inputs relevant order information, the order information module 23 can provide the order information to an order processing module 27. The order processing module 27 can package the order information with the three-dimensional information representative of the anatomical part to create an order file 29. With the order file 29 created; the order processing module 27 can prepare the order file 29 for sending or transmitting and the I/O module 17 send the order file 29 to an intended recipient and/or another location.

Figure 3:
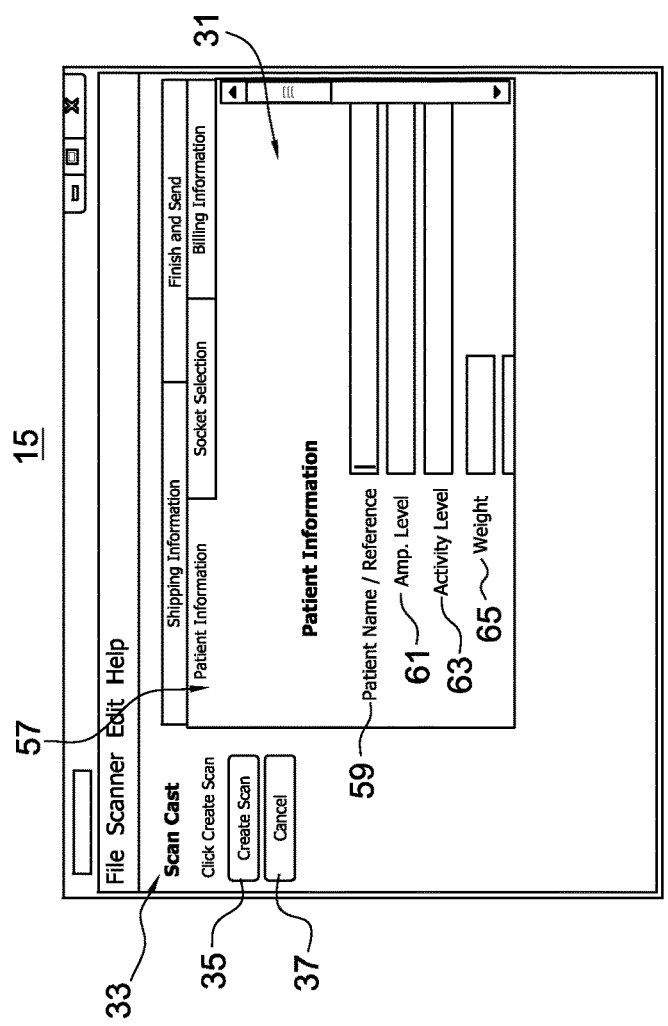
FIG. 3 is an ordering environment according to an embodiment.

FIG. 3 shows an illustration of an ordering environment 15 according to an embodiment. The exemplary ordering environment 15 is an ordering environment for ordering a prosthetic socket for a residual limb. It will be appreciated however that the ordering software 13 can provide a user with an ordering environment for other prosthetic devices and/or orthopedic devices for a variety of anatomical parts. It will be appreciated that the anatomical part can be any suitable body part, including, but not limited, head, neck, torso, shoulder, arm, elbow, wrist, hand, hip, thigh, knee, foot, calf, and the entire body. For instance, the ordering software 13 can provide a user with an ordering environment for cranial orthosis, cervical spine orthosis, cervical orthosis (CO), cervical-thoracic orthosis or CTLSO, thoracic/lumbar/sacral spine (TLSO), shoulder orthosis (SO), humeral fracture orthosis, elbow orthosis (EO), wrist/hand orthosis (WHO), hip orthosis (HO), torso/hip/thigh/knee/foot (HKAFO), knee/ankle/foot orthosis (KAFO), knee orthosis (KO), ground reaction orthosis (GRO), ankle/foot orthosis (AFO), foot orthosis (FO), whole body orthosis (CTLSH-KAFO), and/or any other suitable type of orthopedic device or prosthetic device. By way of another example, the ordering software 13 can provide a user with an ordering environment for a prosthetic liner or check socket.

Referring still to FIG. 3, a user can start an ordering process by selecting an order information option 31 or a scanning option 33. Whatever option is selected by the user, the remaining option can be completed before the ordering process is completed. Optionally, the order environment 15 can include an option for an embedded tutorial including a step-by-step discussion stored in the storage 25 or available to the mobile device 3 through the network 9.

As shown in FIG. 3, the user can select the scanning option 33 and chose to initiate a scanning process. In the example shown here, a "Create Scan" button 35 is selected by the user to initiate the scanning process. Alternatively, the software 13 can initiate the scanning process automatically or in response to feedback information from one or more other sources. For instance, the software 13 can initiate the scanning process in response to feedback information from one or more position sensors associated with the mobile device 3. The scanning processing can also be cancelled by selecting a "Cancel" button 37.

Figure 4:
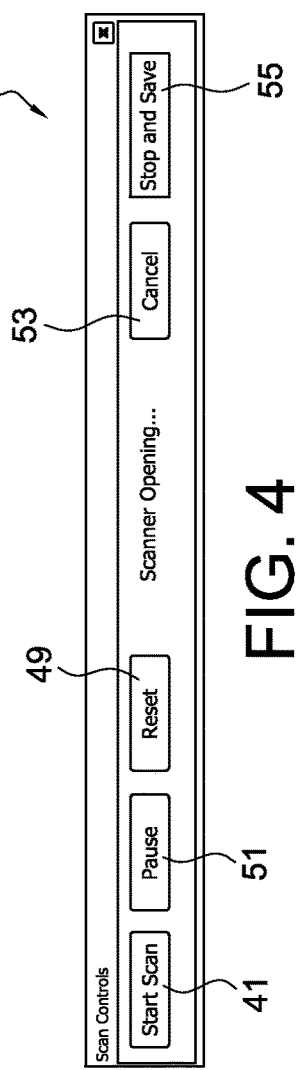
FIG. 4 is an ordering environment according to another embodiment.

Once the scanning process is initiated, the I/O module 17 of the ordering environment 15 can display a scanning control interface 39 as shown in FIG. 4. Optionally, the I/O module 17 can also show a live video feed in the ordering environment 15 with the scanning control interface 39. For instance, a separate window can initiate that shows a live video feed from the perspective of the portable scanner. The separate window can show a landscape view of the area to be scanned.

The scanning control interface 39 can include a "start scan" button 41 through which the I/O module 17 can receive a user input to start a scan. When the user is ready to start scanning, the user can select the "start scan" button 41 such that the I/O module 17 can send the user's request to the imaging module 19. The imaging module 19 can then direct the portable scanner 5 to start scanning the residual limb via the I/O module 17. During scanning, the user can manually move the portable scanner 5 around the residual limb. As the portable scanner 5 is scanning or imaging the residual limb, the imaging module 19 can receive data from the portable scanner 5 via the I/O module 17. Three-dimensional information representative of the residual limb can be obtained from the data by the imaging module 19. Obtaining the three-dimensional information can include the imaging module 19 reading the data, analyzing the data, transforming the data, and/or processing the data.

Figure 5:
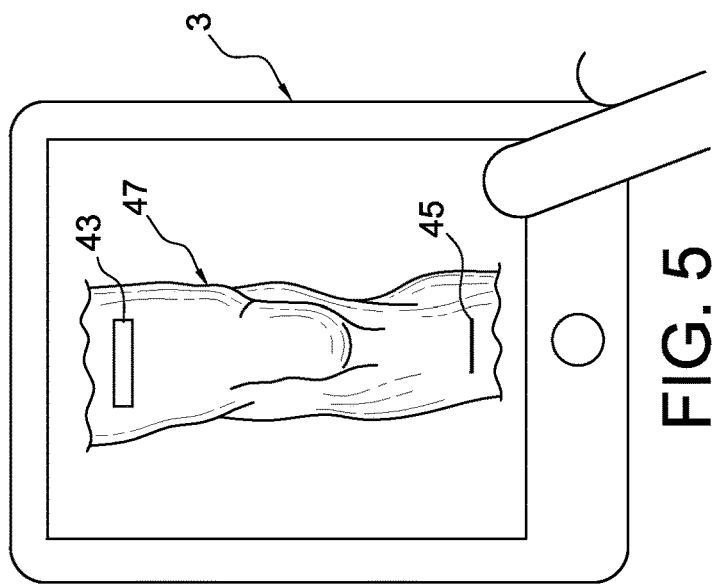
FIG. 5 is an example of the three-dimensional rendered model of an anatomical part displayed on the mobile device.

At least a portion of the three-dimensional information representative of the residual limb can be presented or displayed on the mobile device 3 by the I/O module 17. During the scanning process, the imaging module 19 can generate an image or rendered model of the residual limb from the three-dimensional information. In some embodiments, the data received from the portable scanner 5 can include the image or rendered model of the residual limb. The I/O module 17 can then display the image or rendered model 47 on the mobile device 3 as shown in FIG. 5. Optionally, the image or rendered model can appear on top of the residual limb. The image or rendered model can be displayed in real-time or can be displayed after the residual limb has been scanned or imaged, allowing the user to determine if all areas of interest were captured by the scan. The image or rendered model can be viewed from various angles.

Optionally, markers can be applied to the residual limb prior to scanning. The markers can locate different landmarks such as, but not limited to, the tibial crest and knee center mark. This can provide helpful reference points within the three-dimensional information, model or image. For instance, as seen in FIG. 5, at least one raised marker 43 and/or colored marker 45 applied to the residual limb prior to scanning can be captured in the rendered model or image 47. This advantageously allows the user to determine if the three-dimensional information representative of the residual limb includes specific areas of interest or if the three-dimensional information meets one or more parameters or guidelines. The parameters and/or guidelines may be determined by the user and/or the software 13. Such parameters and/or guidelines may include, for example, but are not limited to, areas of interest, image quality, resolution, control points or landmarks, and statistical values.

If a user makes a mistake during the scanning process or the three-dimensional information fails to meet one or more parameters or guidelines, the user can select the "Reset" button 49 to reset the scan. If the user desires to pause the scan, the user can select the "Pause" button 51 to pause the scan. If the user desires to cancel the scan, the user can select the "Cancel" button 53 to cancel the scan, and data received from the scan can be discarded or deleted.

According to an embodiment, before the user selects the "Start Scan" button 41, the I/O module 17 can display a frame or cube that designates a target area. The L/O module 17 can allow the user to scale the cube by dragging corners of the cube with two or more fingers until the cube encapsulates an area slightly greater than the target area (e.g., the residual limb or anatomical part). The I/O module 17 may highlight a portion of the target area and only direct the portable scanner 5 to scan the area highlighted in red. If the residual limb is not highlighted in red within the target area, the location of the portable scanner 5 relative to the residual limb can be adjusted and/or the cube can be resized.

Once the user selects the "Start Scan" button 41, the I/O module 17 can display a rendered model to the user and the user can begin manually moving or circumferentially positioning the portable scanner 5 around the residual limb to render the scan. The user can move the portable scanner 5 three-hundred and sixty degrees around the residual limb. The user can keep scanning with the portable scanner 5 until the rendered model has encapsulated all desired areas of the target area or residual limb. In some embodiments, the user can circumferentially position the portable scanner 5 completely around the target area or residual limb twice; any sequential passes can improve the accuracy and/or details of the scan.

Through the I/O module 17, the imaging module 19 can instruct the portable scanner 5 to lock onto the target area by default such that subtle movements will not affect the overall scan. The I/O module 17 can instruct the user to stay at least two-feet from the target area and to move in slow steady movements, helping to maintain the tracking lock. If a movement is too drastic, the I/O module 17 can prompt the user with an error message saying "Tracking Lost." In that case, the user can select the "Reset" button 49 to reset the scan.

The scanning control interface 39 can include a "Stop and Save" button 55 through which the I/O module 17 can receive a user input to stop and/or save the scan. When everything is deemed captured, the user can select the "Stop and Save" button 55. The I/O module 17 can convey the user's request to the imaging module 19, which can direct the portable scanner 5 to stop scanning and send at least a portion of the three-dimensional information to the order processing module 27 for holding in the storage 25. As explained above, the three-dimensional information may include the image or rendered model. In some embodiments, once the scanning process is stopped, the I/O module 17 can display a review screen within the ordering environment 15 through which the user can review the image or rendered model generated by the scanning process. If the image or rendered model is satisfactory, the user can select the "Stop and Save" button 55 again and the imaging module 19 can provide at least a portion of the three-dimensional information to the order processing module 27, which, in turn, can provide it to the storage 25 to be temporarily held or saved. If the image or rendered model is unsatisfactory, the scanning process can be cancelled and/or reset.

Generating the three-dimensional information representative of the residual limb 47 using the at least one portable scanner 5 and mobile device 3, advantageously provides more accurate fitting information than in the prior art, substantially decreasing the likelihood of a poor fitting prosthetic socket. It also avoids the discomfort and inconveniences that can result when plaster casts are made of the residual limb. This also eliminates the need to convert information obtained from a physical mold to three-dimensional information representative of the residual limb, which, in turn, reduces labor, cost, and time.

Generating the three-dimensional information using the portable scanner 5 and the mobile device 3 also provides the user and/or patient significant freedom. For instance, the mobile device 3 and the portable scanner 5 can be used to generate the three-dimensional information at a patient's home, in a hospital room, at a community center, in a remote location, at different clinics in a single day, in third-world countries, on humanitarian missions, in vehicles, off the power grid, and in other settings. This is advantageous over the prior art where the patient is required to visit a designated facility with big, cumbersome, and stationary equipment to be fitted for a custom prosthetic or orthopedic device, requiring significant time and money and in many instances proving impossible for patients living in remote locations.

Optionally, the order environment 15 can include an option for the user to manipulate, modify, and/or edit the three-dimensional information (including the image or rendered model). This can occur either before or after the three-dimensional information is saved in the storage 15. The software 13 may allow the user to, for example, smooth the rendered model, resize the rendered model, align the rendered model, and/or perform other similar functions.

It will be appreciated that in other embodiments, the software 13 can automatically initiate and/or stop the scanning process independent of user input. For instance, the imaging module 19 can analyze or scan the three-dimensional information to determine if one or more parameters or guidelines have been met and stop the scan if the one or more parameters or guidelines are met.

In some embodiments, the scanning process can include calibration of the portable scanner 5. For instance, when the "Create Scan" button is selected by the user, the I/O module 17 can convey the user's request to the imaging module 19, which can set the portable scanner 5 to specific settings such as a specific resolution, zoom, color setting, alignment, position, or other appropriate setting. Alternatively, preferred portable scanner settings can be in text within the software 13, and calibration is manually performed by the user. The preferred settings may be displayed prior to or during the scanning process. The preferred settings can also be displayed and included in a help section of the software 13.

Figures 6, 7, 8:
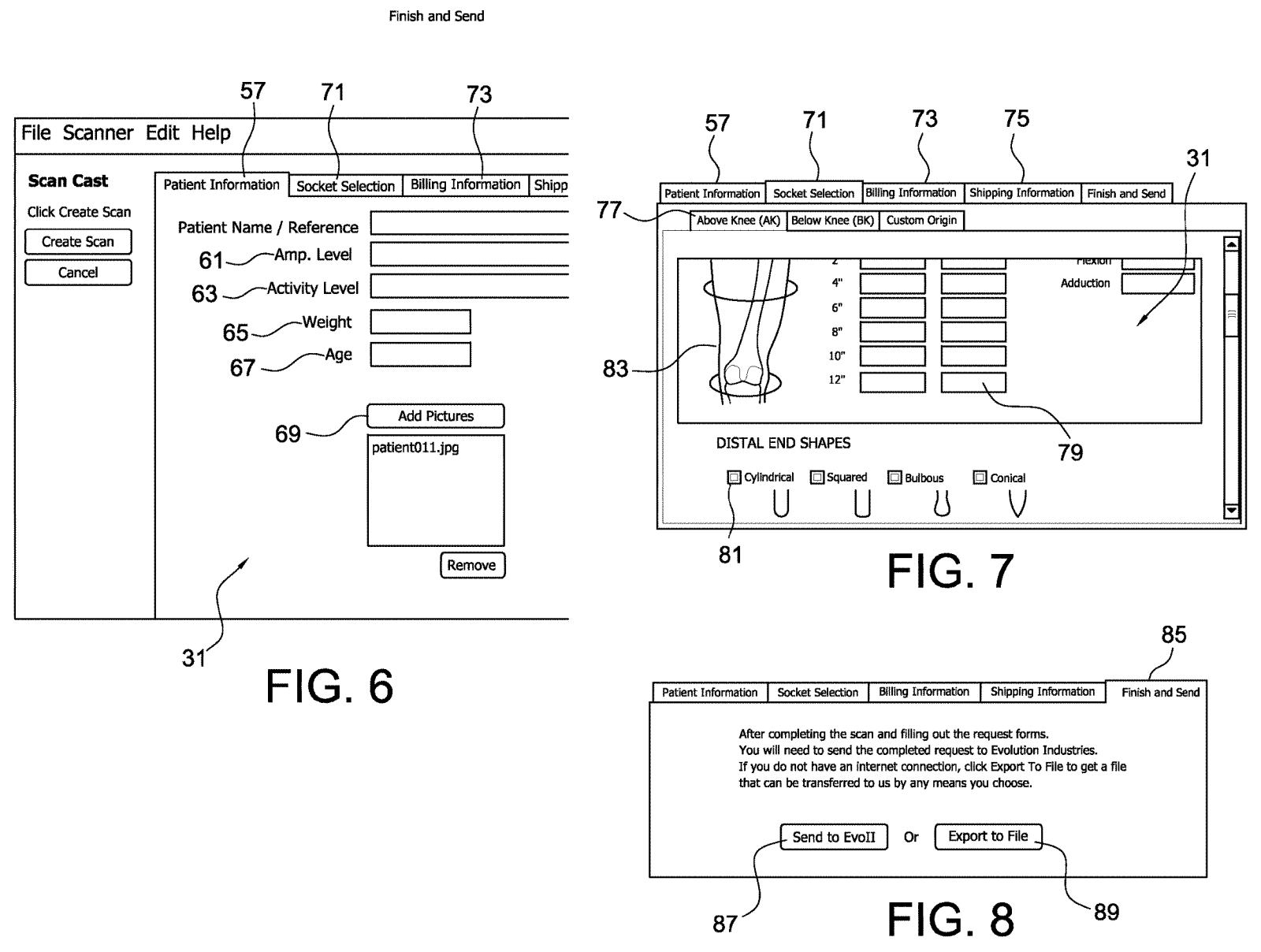

After the scanning process is complete or before the scanning process is initiated, the user can select the order information option 31 as shown in FIGS. 6 and 7. In the example shown, the ordering environment 15 can provide the user with a variety of different options, including, but not limited to, a patient information tab 57, a socket selection tab 71, a billing information tab 73, and a shipping information tab 75. When receiving inputs from a user, the I/O module 17 can communicate relevant commands to the order information module 23.

Information can be entered or made accessible through pre-defined menus, pre-populated fields, look ups, text fields, combinations thereof, or any other suitable means. Through the order information option 31, the user is able to submit specific details regarding the order along with any other necessary information and/or documents. For instance, a "Billing Information" tab 73 can make one or more fields, available, through which the user can enter billing information such as, but not limited to, mailing address, payment information, and reimbursement information. A "Shipping Information" tab 75 can make one or more fields, available through which the user can enter shipping information such as, but not limited to, user or patient name, mailing address, telephone number, and email.

The order information module 23 can also receive instructions relating to patient information that a user wants to input into the software 13. In the example shown here, a "Patient Information" tab 57 is selected by the user to begin entering patient information as seen in FIG. 6. Once the "Patient Information" tab is selected 57, the I/O module 17 can display a variety of different fields through which the user can enter patient information. For instance, text fields (shown in FIGS. 3 and 6) can include, but are not limited to, patient name/reference field 59, amputation level field 61, activity level field 63, weight field 65, and field age 67. While or after the patient information is being entered, the order information module 23 can store all or part of the patient information in the storage 25. After the patient information is received, the order information module 23 can create partial order file in an encrypted format. Other security measures may also be taken to protect the patient information under HIPAA regulations.

Optionally, the ordering environment 15 can include an "Add Pictures" button 69, allowing the user to upload one or more image files 69 into the software 13. Such image files may be of the patient and/or residual limb and may be used, for example, by an intended recipient or fabricator to verify the accuracy of the three-dimensional information.

As seen in FIG. 7, the order information module 23 can also receive instructions relating to socket selection information that the user wants to input into the software 13. A "Socket Selection" tab 71 can be selected by the user to begin entering socket information. Once the "Socket Selection" tab 71 is selected, the I/O module can display a variety of different fields through which the user can enter socket selection information. For instance, the fields can include, but are not limited to, tabs 77 associated with different amputation types, measurement fields 79, distal end shape option fields 81, and anatomical illustrations 83. In other embodiments, the order information module 23 can receive at least some socket selection information from the order processing module 27 and/or the imaging module 19. For instance, the order processing module 27 and/or the imaging module 19 can process the three-dimensional information using a visual limb recognition algorithm to automatically generate at least some of the socket selection information such as, for example, measurements and distal end shapes.

In some embodiments, order information can be obtained from other sources than the user. For instance, at least some of the order information can be obtained through the internet or other database associated with a healthcare network, a medical professional office, a clinic, a fabricator, a seller, or another source.

Once the order information is received by the software 13, the order information module 23 can provide all or some of the order information to the order processing module 27, which can then provide it to the storage 25 to be temporarily held or saved. Optionally, when the order information process and the scanning process are complete, the software 13 can present or display the order information and the three-dimensional information to the user for review. In an embodiment, the user can edit one or portions of the order information and/or three-dimensional information with the changes made during review saved in the storage.

The ordering environment 15 can include a "Finish and Send" tab 85 (best seen in FIG. 8) through which the I/O module can receive a user input to complete and send the order. When the user is ready to finish and send the order, the user can selected the "Finish and Send" tab 85 such that the I/O module 17 can send the user's request to the order processing module 27. The order processing module 27 can then prepare and/or package the order information and at least a portion of the three-dimensional information into an order file 29. At least a portion of the order information and at least a portion of the three-dimensional information can be linked, packaged, embedded, or compiled together into the order file 29. This advantageously eliminates the need to manually enter or record the three-dimensional information at multiple locations, which, in turn, shortens the overall time to complete the ordering of a prosthetic or orthopedic device. Optionally, the order file 29 can be saved before sending or transmitting.

Further, the order file 29 can be password protected and/or encrypted by the order processing module 27 and/or the I/O module 17, protecting the patient's privacy. In an embodiment, the order processing module 27 can format the order file 29 in an encrypted file format (e.g. an .EVO file format) that only an intended recipient of the order is capable of deciphering private and/or necessary details from the order file 29 for fabrication. In other embodiments, the order processing module 27 and/or the I/O module 17 can encase the order file 29 in an encrypted intelligent shell, allowing only the intended reception to access the material within the order file 29.

The order processing module 27 can provide the user with the option of transmitting the order file 29 directly to the intended recipient or to export the order file 29 to receive a file that can be transferred to the intended recipient by other means. The user can select, for example, a "Send to EvoII" button 87 to send the order file 29 to the intended recipient. The user can select an "Export to File" button 89 to receive a file including the order file 29.

When the user selects the "Send to EvoII" button 87, the I/O module can send the order file 29 electronically to the intended recipient. The intended recipient can be an orthosis and/or prosthesis fabricator, a medical professional, another computer device, a web server, a cloud server, or the computer system 7 at a remote facility 11. In some embodiments, the intended recipient can use the order file 29 to obtain fitting information. The intended recipient then can form or fabricate a prosthetic socket according to the fitting information obtained from the order file 29. It will be appreciated that the entire ordering process can be completed in minutes rather than hours and/or days as in the prior art. Moreover, the fitting information obtained from the order file 29 is more accurate than fitting information obtained from a plaster cast, providing a better fit for the patient.

Electronically transmitting the order file 29 (including both order and three-dimensional information) also eliminates potential postal delays and the need to manually and/or repeatedly enter or record information at multiple locations, which, in turn, shortens overall production time. Electronically transmitting the order file 29 also eliminates the likelihood of a plaster cast deforming during transport, which, in turn, can generate faulty fitting information and a poor fit.

The order file 29 can be sent to the recipient using an FTP server. The order file 29 can be sent as an attachment in an email. The order file 29 can be automatically attached to the email by the I/O module 17. The email can be from a specific email address linked to the software 13. Upon receipt, the attached order file 29 can only be interpreted by the intended recipient. Optionally, the I/O module 17 can send the order file 29 in the email and can automatically populate fields in the email based on data in the order file 29. At least a portion of the order information in the order file 29 can be inserted in the body of the email while at least a portion of the three-dimensional information is attached to the email.

The intended recipient and/or the I/O module 17 can display or send a notification to the user to confirm receipt and/or transmission of the order file 29. Optionally, the notification from the intended recipient can include a representation of the three-dimensional information included in the order file 29 such that the user can confirm that the order file 29 was not corrupted or altered during transmission.

The system 1 can thus provide a user and/or patient with the freedom to order custom prosthetic and orthopedic devices almost anywhere. For instance, a user can create an order for a prosthetic device at the patient's home, in a hospital room, at a community center, in a remote location, in third-world countries, on humanitarian missions, in vehicles, off the power grid, and in other settings. This is advantageous over the prior art where the patient is required to visit a designated facility with big, cumbersome, and stationary equipment to be fitted for a custom prosthetic or orthopedic device, requiring significant time and money and in many instances proving impossible for patients living in remote locations.

In addition to the foregoing, one will appreciate that embodiments of the present disclosure can also be described in terms of flowcharts including one or more steps for accomplishing a particular result. For example, the steps of FIGS. 9 and 10 and the corresponding text describe steps in a method for ordering a custom prosthetic or orthopedic device. The steps of FIGS. 9 and 10 are described below with respect to the components and modules of FIGS. 1-8.

Figure 9:
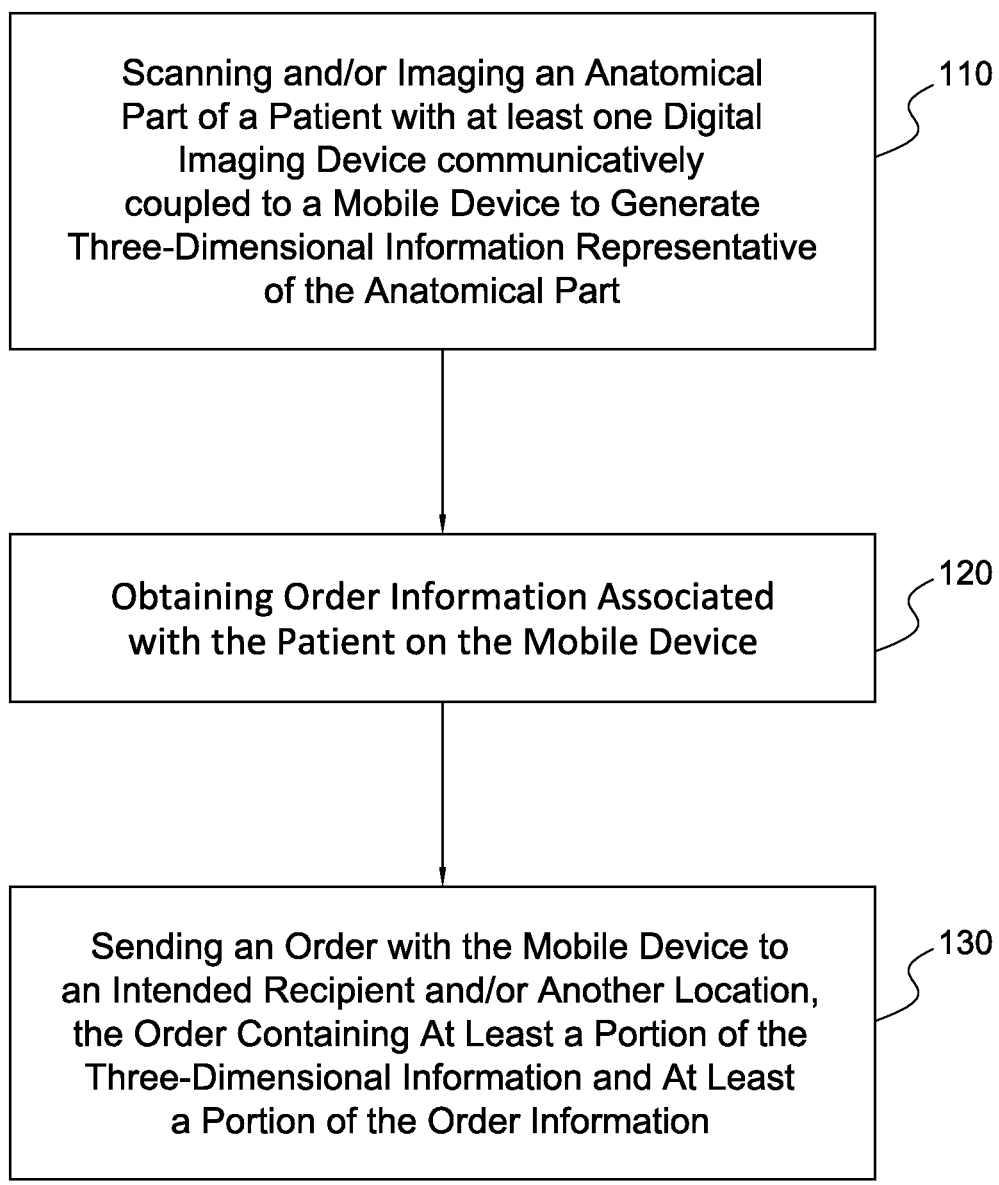
FIG. 9 is an overview of the steps in an embodiment of the custom prosthetic or orthopedic device ordering method.
Figure 10:
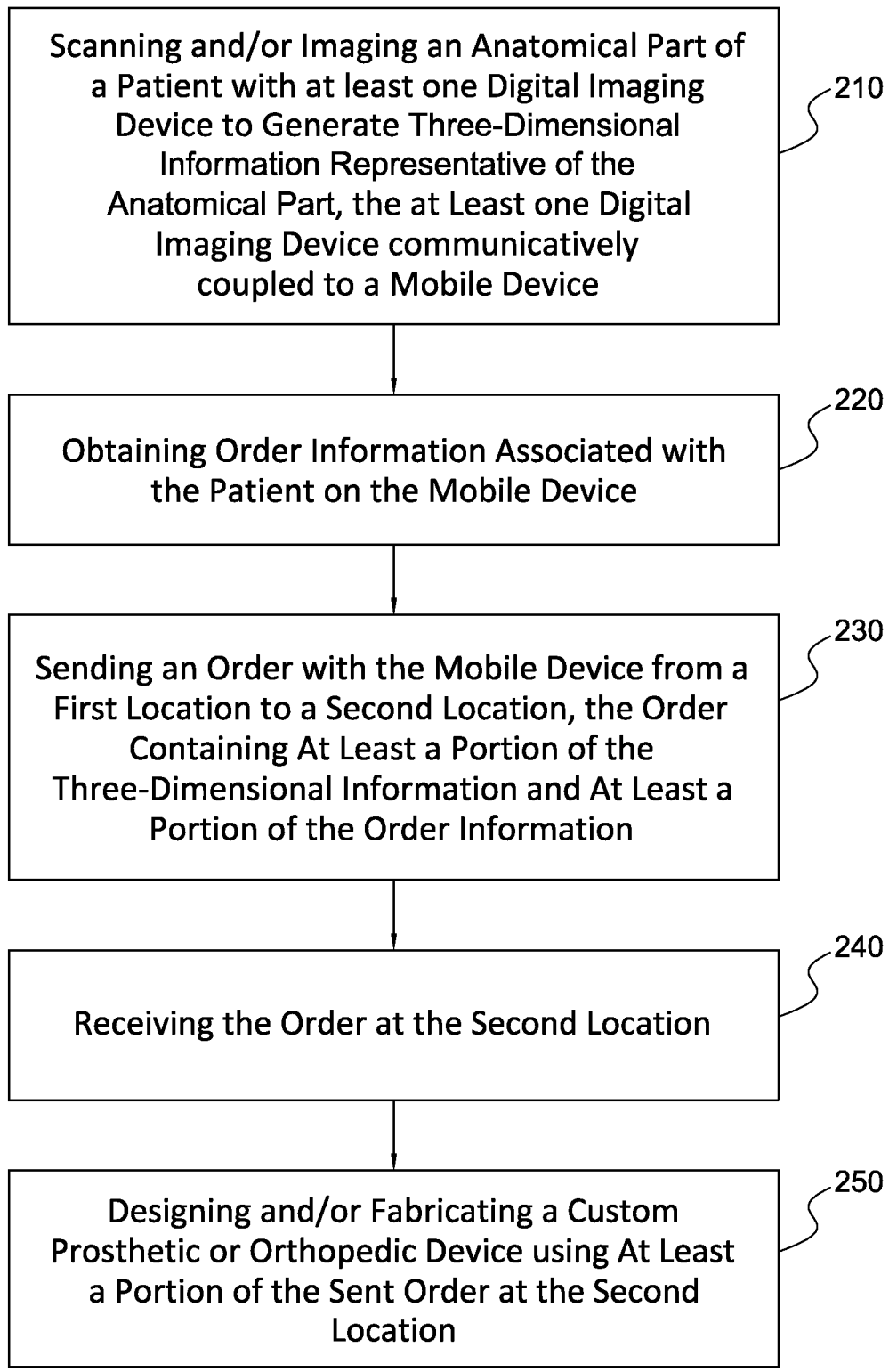
FIG. 10 is an overview of the steps in another embodiment of the custom prosthetic or orthopedic device ordering method.

For instance, FIG. 9 illustrates a method 100 in accordance with the present disclosure for ordering a custom prosthetic or orthopedic device includes step 110 of scanning and/or imaging an anatomical part of a patient with at least one digital imaging device or portable scanner communicatively coupled to a mobile device to generate three-dimensional information representative of the anatomical part. Step 110 can include receiving user input specifying the initiation of a scan by the portable scanner. For example, FIGS. 3-5 and the accompanying description depict and describe an interface for displaying options for scanning an anatomical part with a portable scanner communicatively coupled to a mobile device and ordering software. To scan the anatomical part, a user can manually move or adjust the portable scanner about the anatomical part to generate the three-dimensional information.

FIG. 9 also shows that the method can include the step 120 of obtaining order information associated with the patient on the mobile device. Step 120 can include receiving user input containing order information. For example, FIGS. 6 and 7 and the accompanying description depict and describe an interface for displaying options for obtaining order information associated with the patient on the mobile device.

Additionally, FIG. 9 shows that the method 100 can include a step 130 of sending or transmitting an order with the mobile device to an intended recipient and/or another location. The order contains at least a portion of the three-dimensional information and at least a portion of the order information. Step 130 can include transmitting an order file electronically to the intended recipient such as a fabricator at another location. For instance, FIGS. 1 and 8 and the accompanying description depict and describe an interface and system where a user can send an order file electronically from the mobile device to an intended recipient via a network. The order file contains order information and three-dimensional information. Creating the order file with the portable scanner and mobile device can be performed virtually anywhere. This advantageously provides a user and/or patient with significant freedom. For instance, the order file can be created at the patient's home, in a hospital room, in a community center, in the field, on a humanitarian mission, off the power grid, and/or in other settings around the world, substantially eliminating the need of extensive facilities.

As an additional example, FIG. 10 illustrates that a method 200 in accordance with the present disclosure for ordering a custom prosthetic or orthopedic device includes steps 210, 220, and 230, which are similar to steps 110, 120, 130. The method can further include a step 240 of receiving the order a second location. Step 240 can include sending or transmitting an order file electronically from the mobile device to a fabricator at a second location. For instance, FIGS. 1 and 8 and the accompanying description depict and describe an interface and system where the intended recipient at the second location can receive the order file.

Further, FIG. 10 also shows that the method can include a step 250 of designing and/or fabricating a custom prosthetic or orthopedic device using at least a portion of the sent order at the second location. Step 250 can include the intended recipient obtaining fitting information from the sent order and then forming a prosthetic device or orthotic device according to the fitting information. FIGS. 1 and 8 and the accompanying description depict and describe an interface and system where the intended recipient at the second location can design and/or fabricate a prosthetic or orthopedic device using the order file.

Accordingly, FIGS. 1-10 provide a number of components, schematics and mechanisms for allowing a user to order a custom prosthetic or orthopedic device. The user can do so in a versatile, affordable, and portable manner. The user can also generate more accurate fitting information for use in the design and/or fabrication of the device.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, or a combination, all of which can be behaviorally equivalent. Modules may be implemented using computer hardware in combination with software routine(s) written in a computer language. It may be possible to implement modules using physical hardware that incorporates discrete or programmable analog and/or digital hardware. Examples of programmable hardware include computers, microcontrollers, microprocessors, application-specific integrated circuits, field programmable gate arrays, and complex programmable logic devices.

As noted above, the software may be embodied on a computer readable medium which when executed by a processor component of a computer device performs a sequence of steps. The application may be a mobile application or application software configured to run on smartphones, tablets computers, and/or other mobile devices. Moreover, embodiments of the present disclosure may comprise or utilize a special-purpose or general-purpose computer system that includes computer hardware, such as, for example, one or more processors and system memory, as discussed in greater detail below. Embodiments within the scope of the present disclosure also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the disclosure can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the disclosure.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the disclosure may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud computing model can be composed of various characteristics, such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth.

Some embodiments, such as a cloud computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

It will be appreciated that the order can be sent from a first location, to a second location, to a third location, and/or any other suitable number of locations. For instance, the order can be sent from the mobile device to a web server at a second location, and then to a cloud server at a third location for storage, processing and/or access by another computer device. Electronically transmitting the order can thus make the order readily accessible to any number of authorized and/or intended recipients.

The patient and user can be the same individual or the patient and the user can be different individuals. The user can be a medical professional, a clinician, a prosthetist, an orthotist, or any other suitable individual. The user can comprise one or a plurality of individuals. While the computer device is described as a mobile device, in other embodiments, the computer device can be general purpose computer, a personal computer, a special purpose computer, or any other suitable type of computer device.

While the digital imaging device is described as a portable scanner, in other embodiments, the digital imaging device can be a RGB color VGA video camera and one or more depth sensors, a three-dimensional imaging scanner, a laser scanner, a digital camera with one or more motion measurement sensors, a mechanical digitizer, a device using structure light projection, a contact handheld digitizer, an infrared projector, an infrared camera, a color camera, combinations thereof, or any other suitable digital imaging device. The digital imaging device may include simultaneous localization and mapping, or SLAM.

It will be appreciated that the I/O module can be configured to enable the mobile or computer device to receive data and/or instructions through different input components such as, but not limited to, a keyboard, a mouse, microphone, a joystick, a satellite dish, and/or other appropriate input devices. The I/O module can also be configured to enable the computer device to output data and/or information through different output components such as, but not limited to, a monitor, a speaker, a printer, or the like. A particular output component may be integrated with or peripheral to the computer device.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A method of ordering a custom prosthetic device, comprising the steps of:
providing a portable scanner communicatively coupled to a mobile device routinely carried by a user and including an ordering software application arranged to provide and display a frame on the mobile device having an adjustable configuration for designating a target area on a residual limb of a patient;
the user manipulating the frame displayed by the ordering software application on the mobile device to designate the target area on the residual limb;
manually moving the portable scanner about the residual limb to generate three-dimensional information representative of the residual limb via the ordering software application, wherein the ordering software application directs the portable scanner to lock onto and scan only the residual limb within the target area when the user moves the portable scanner about the residual limb;
uploading one or more images of the residual limb via the ordering software application to verify an accuracy of the three-dimensional information;
obtaining order information associated with the patient via the ordering software application, wherein the ordering software application processes the three-dimensional information to identify a distal end shape of the residual limb and to automatically display socket selection information on the mobile device;
rendering on the mobile device or computer system the three-dimensional information to create a three-dimensional model of the residual limb;
displaying, in real-time, a rendered three-dimensional model on the mobile device, during movement of the portable scanner about the residual limb; and
transmitting an order with the mobile device to an intended recipient, the order containing at least a portion of the three-dimensional information and at least a portion of the order information.

2. The method of claim 1, further comprising packaging the three-dimensional information and the order information together in the order before transmitting the order with the mobile device.

3. The method of claim 1, further comprising encrypting the order on the mobile device before transmitting the order to the intended recipient.

4. The method of claim 3, wherein manually moving the portable scanner about the residual limb includes manually moving the portable scanner circumferentially about the residual limb at a home of the patient.

5. The method of claim 3, wherein manually moving the portable scanner about the residual limb includes manually moving the portable scanner circumferentially about the residual limb at a hospital room of the patient.

6. The method of claim 1, wherein the mobile device comprises a laptop computer.

7. The method of claim 1, further comprising obtaining fitting information for the patient from the order.

8. The method of claim 1, wherein the portable scanner comprises a three-dimensional sensor.

9. The method of claim 1, further comprising:
verifying the accuracy of the three-dimensional information;
transmitting the three-dimensional information if the accuracy of the three-dimensional information satisfies one or more parameters comprising areas of interest, image quality, resolution, control points, control landmarks, or statistical values; and
resetting the portable scanner by restarting the scan if the accuracy of the three-dimensional information fails to satisfy the one or more parameters.

10. The method of claim 1, wherein transmitting the order to the intended recipient includes transmitting the order from the mobile device from a first location to the intended recipient at a second location.

11. The method of claim 1, further comprising manipulating the three-dimensional information on the mobile device before transmitting the order.

12. The method of claim 10, further comprising fabricating a custom prosthetic device at the second location using at least a portion of the order.

13. The method of claim 10, further comprising transmitting a representation of the three-dimensional information from the second location to the mobile device at the first location.

14. A portable system for ordering a custom prosthetic device, comprising:
 a hand-held scanner arranged to capture a three-dimensional scan of a residual limb, the hand-held scanner being manually adjustable about the residual limb; and
 a mobile device routinely carried by a user and communicatively coupled to the hand-held scanner, the mobile device including an ordering software application arranged to provide and display a frame having an adjustable configuration for designating a target area on the residual limb, and obtain the three-dimensional scan from the portable scanner and package order information with the three-dimensional scan in an order;
 wherein the ordering software application directs the portable scanner to lock onto and only scan only the residual limb within the target area when the user moves the portable scanner about the residual limb, and processes the three-dimensional information to automatically generate and display socket selection information including an identification of a distal end shape of the residual limb on the mobile device;
 rendering on the mobile device or computer system the three-dimensional information to create a three-dimensional model of the residual limb; and
 displaying, in real-time, a rendered three-dimensional model on the mobile device, during movement of the portable scanner about the residual limb.

15. The system of claim 14, wherein the mobile device is arranged to transmit the order to a computer system via a network, wherein the computer system is located remotely from the mobile device.

16. The system of claim 15, wherein the ordering software application encrypts the order before transmitting the order to the computer system.

17. The system of claim 15, wherein the ordering software application is arranged to generate a three-dimensional model of the anatomical limb from the three-dimensional scan.

18. A method of ordering a custom prosthetic device, comprising the steps of:
 providing a portable scanner communicatively coupled to a mobile device routinely carried by a user and including an ordering software application arranged to provide and display a frame having an adjustable configuration for designating a target area on a residual limb of a patient;
 manipulating the frame displayed by the ordering software application on the mobile device to designate the target area on the residual limb;
 manually moving the portable scanner about the residual limb to generate three-dimensional information representative of the residual limb via the ordering software application wherein the ordering software application directs the portable scanner to lock onto and scan only the residual limb within the target area when the user moves the portable scanner about the residual limb;
 uploading one or more images of the residual limb via the ordering software application to verify an accuracy of the three-dimensional information;
 obtaining order information associated with the patient via the ordering software application, wherein the ordering software application processes the three-dimensional information to automatically generate and display socket selection information including an identification of a distal end shape of the residual limb on the mobile device;
 wherein the ordering software application provides a user with one or more of the following order environments; cranial orthosis, cervical spine orthosis, cervical orthosis, cervical-thoracic orthosis or, thoracic/lumbar/sacral spine, shoulder orthosis, humeral fracture orthosis, elbow orthosis, wrist/hand orthosis, hip orthosis, torso/hip/thigh/knee/foot, knee/ankle/foot orthosis, knee orthosis, ground reaction orthosis, ankle/foot orthosis, foot orthosis, whole body orthosis, and/or any other suitable type of orthopedic device or prosthetic device;
 transmitting an order with the mobile device from a first location to a second location, the order containing at least a portion of the three-dimensional information and at least a portion of the order information;
 receiving the order at the second location;
 fabricating a custom prosthetic device using at least a portion of the order at the second location;
 rendering on the mobile device or computer system the three-dimensional information to create a three-dimensional model of the residual limb; and
 displaying, in real-time, a rendered three-dimensional model on the mobile device, during movement of the portable scanner about the residual limb;
 wherein an image of the rendered three-dimensional model can appear on top of an image of the residual limb within the ordering software application.

19. The method of claim 1, wherein the ordering software application can provide a user with an ordering environment for cranial orthosis, cervical spine orthosis, cervical orthosis, cervical-thoracic orthosis or, thoracic/lumbar/sacral spine, shoulder orthosis, humeral fracture orthosis, elbow orthosis, wrist/hand orthosis, hip orthosis, torso/hip/thigh/knee/foot, knee/ankle/foot orthosis, knee orthosis, ground reaction orthosis, ankle/foot orthosis, foot orthosis, whole body orthosis, and/or any other suitable type of orthopedic device or prosthetic device.

20. The method in claim 1, wherein an image of the rendered three-dimensional model can appear on top of an image of the residual limb within the ordering software application.

21. The method of claim 1, wherein raised or colored markers are directly applied to a tibial crest and to a knee center of the residual limb in order to assist the portable scanner in locating different features.

* * * * *